(12) United States Patent
Simundic

(10) Patent No.: US 11,305,093 B2
(45) Date of Patent: Apr. 19, 2022

(54) CANNULA

(71) Applicant: Xenios AG, Heilbronn (DE)

(72) Inventor: Ivo Simundic, Wendlingen (DE)

(73) Assignee: Xenios AG, Heilbronn (DE)

( * ) Notice: Subject to any disclaimer, the term of this patent is extended or adjusted under 35 U.S.C. 154(b) by 491 days.

(21) Appl. No.: 15/568,035

(22) PCT Filed: Apr. 21, 2016

(86) PCT No.: PCT/DE2016/000172
§ 371 (c)(1),
(2) Date: Oct. 20, 2017

(87) PCT Pub. No.: WO2016/169547
PCT Pub. Date: Oct. 27, 2016

(65) Prior Publication Data
US 2018/0110963 A1    Apr. 26, 2018

(30) Foreign Application Priority Data

Apr. 21, 2015  (DE) .................. 10 2015 005 002.8

(51) Int. Cl.
*A61M 25/00* (2006.01)
*A61M 5/32* (2006.01)

(52) U.S. Cl.
CPC ...... *A61M 25/0068* (2013.01); *A61M 25/007* (2013.01); *A61M 25/0075* (2013.01); *A61M 5/3286* (2013.01); *A61M 2025/0073* (2013.01)

(58) Field of Classification Search
CPC ............ A61M 25/007; A61M 25/0068; A61M 25/0023; A61M 25/0075; A61M 2025/0018; A61M 2025/0073
See application file for complete search history.

(56) References Cited

U.S. PATENT DOCUMENTS

| 4,639,252 A | 1/1987 | Kelly et al. |
| 4,661,094 A * | 4/1987 | Simpson ............... A61B 17/22 604/8 |
| 5,085,635 A | 2/1992 | Cragg |
| 5,171,218 A | 12/1992 | Fonger et al. |
| 5,616,137 A * | 4/1997 | Lindsay ............. A61M 25/007 604/264 |
| 6,044,845 A | 4/2000 | Lewis |

(Continued)

FOREIGN PATENT DOCUMENTS

| CN | 1443580 A | 9/2003 |
| CN | 2616215 Y | 5/2004 |

(Continued)

OTHER PUBLICATIONS

International Search Report of PCT/DE2016/000172, dated Oct. 27, 2016.

(Continued)

*Primary Examiner* — Nathan R Price
*Assistant Examiner* — Anh Bui
(74) *Attorney, Agent, or Firm* — Collard & Roe, P.C.

(57) ABSTRACT

The invention relates to a cannula comprising a tip and an outlet, the cannula having a reduction in the internal diameter, which reduction is designed as a conically tapering tip the end of which has a length that is shorter than the internal diameter of the adjoining portion of the cannula.

13 Claims, 2 Drawing Sheets

(56) References Cited

U.S. PATENT DOCUMENTS

| | | | |
|---|---|---|---|
| 2003/0171721 A1 | 9/2003 | Enomoto et al. | |
| 2004/0037986 A1* | 2/2004 | Houston | A61F 2/844 428/36.9 |
| 2004/0102734 A1 | 5/2004 | Yozu et al. | |
| 2010/0114017 A1* | 5/2010 | Lenker | A61B 17/1214 604/96.01 |
| 2010/0211008 A1 | 8/2010 | Wiest et al. | |
| 2010/0268017 A1 | 10/2010 | Siess | |
| 2011/0160517 A1* | 6/2011 | Smith | A61M 1/3653 600/16 |
| 2011/0166589 A1 | 7/2011 | Morningstar | |
| 2012/0245562 A1 | 9/2012 | Bihlmaier | |
| 2013/0090608 A1 | 4/2013 | Stout et al. | |
| 2014/0336559 A1 | 11/2014 | Heilman et al. | |
| 2015/0359998 A1* | 12/2015 | Carmel | A61M 25/003 604/509 |
| 2016/0129170 A1 | 5/2016 | Siess | |

FOREIGN PATENT DOCUMENTS

| | | |
|---|---|---|
| CN | 201026340 Y | 2/2008 |
| CN | 201257222 Y | 6/2009 |
| CN | 201658732 U | 12/2010 |
| CN | 201855492 U | 6/2011 |
| CN | 202724337 U | 2/2013 |
| CN | 202951099 U | 5/2013 |
| DE | 196 05 864 A1 | 8/1996 |
| DE | 103 36 902 B3 | 8/2004 |
| JP | H10-052489 A | 2/1998 |
| JP | 2000-512184 A | 9/2000 |
| JP | 2002-533157 A | 10/2002 |
| JP | 2003-534828 A | 11/2003 |
| JP | 35-29822 B2 | 5/2004 |
| JP | 2013-081725 A | 5/2013 |
| WO | 99/37351 A1 | 7/1999 |
| WO | 99/37352 A1 | 7/1999 |
| WO | 00/38591 A2 | 7/2000 |
| WO | 03/041782 A1 | 5/2003 |
| WO | 2005/016416 A1 | 2/2005 |
| WO | 2014/065969 A1 | 5/2014 |
| WO | 2014/113257 A2 | 7/2014 |

OTHER PUBLICATIONS

Japanese Office Action dated Jan. 18, 2022 in Japanese Application No. 2021-065474 with English translation.

* cited by examiner

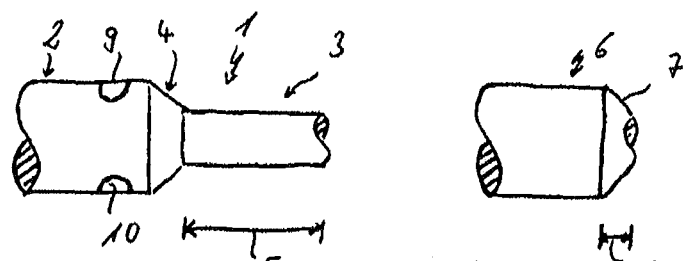
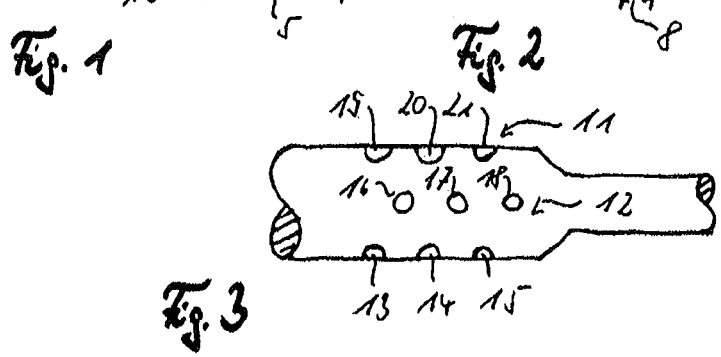
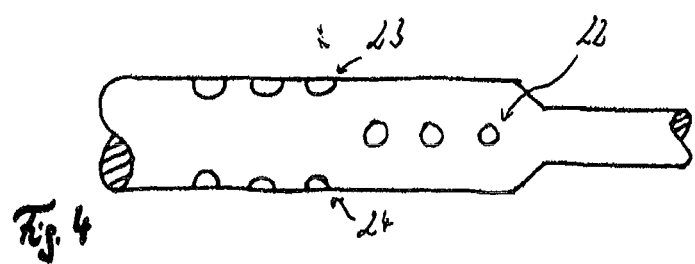
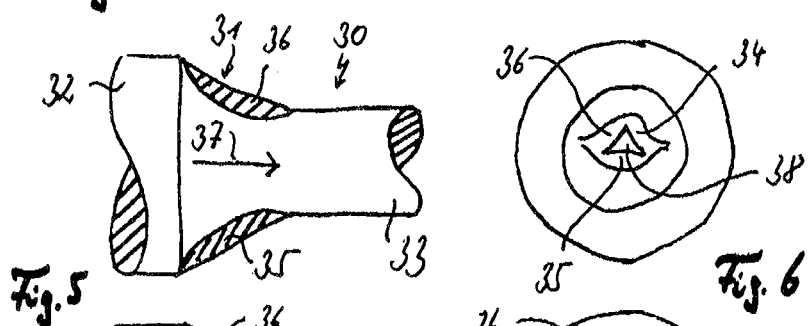
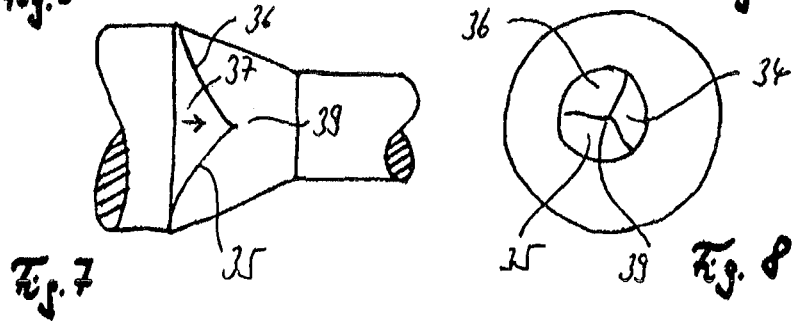

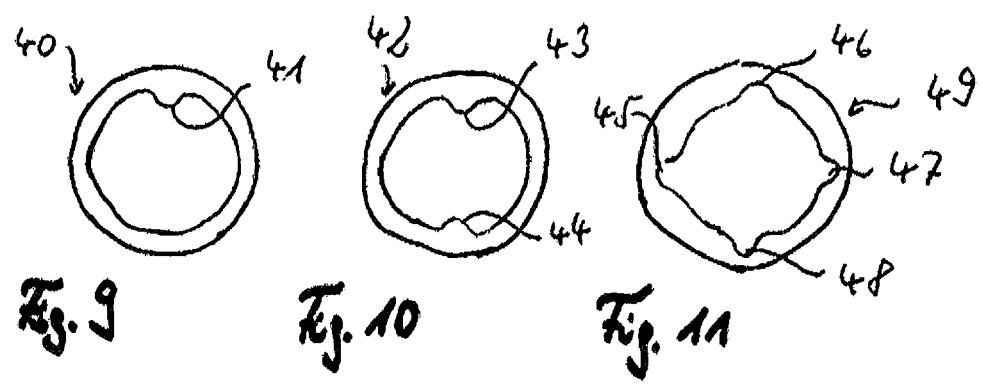

CANNULA

CROSS REFERENCE TO RELATED APPLICATIONS

This application is the National Stage of PCT/DE2016/000172 filed on Apr. 21, 2016, which claims priority under 35 U.S.C. § 119 of German Application No. 10 2015 005 002.8 filed on Apr. 21, 2015, the disclosure of which is incorporated by reference. The international application under PCT article 21(2) was not published in English.

The invention relates to a cannula with a syringe and an outlet. Such cannulas are used in particular as arterial cannulas. There are available in different diameters and lengths.

The object of the invention is to further develop such cannulas.

According to a first aspect of the invention this object is achieved in that the internal diameter of the cannula is reduced.

The reduction in the internal diameter can be in the form of a conically tapering tip. In this case it can be advantageous if the conical end of the tip has a length that is shorter than the internal diameter of the area of the cannula adjoining it.

The reduction in the internal diameter can also be in the form of a caliber narrowing between two cylindrical cannula sections with different diameters.

In this case it is advantageous if the reduction in the internal diameter is located at a distance of 25% to 40%, preferably around 30%-35% of insertion length away from the tip of the cannula. In an advantageous example of embodiment the tapering starts after around two thirds of the cannula or insertion length.

A preferred insertion length of the cannula is around 20-50 cm, preferably between 28 and 45 cm. This makes several application variants possible, depending on the length. A short insertion length allows application below the renal artery and a long insertion lengths permits application above or at the rental artery.

Depending on the reduction of the diameter sudden changes in caliber come about which can exhibit a Delta of 2 Fr 4 Fr for example. Examples of relevance to practice are 15 Fr to 13 Fr, 17 Fr to 15 Fr, 17 Fr to 13 Ft, 19 Fr to 17 Fr and 19 Fr to 15 Fr.

Such a reduction in the internal diameter of a cannula results in a jet current at the cannula tip, in the short insertion length or in the cannula section with the reduced diameter.

An advantageous variant of embodiment of the cannula envisages that it has lateral holes and the reduction diameter is arranged between the lateral holes and the tip of the cannula. Through the arrangement of such holes in the cannula perfusion of the lower extremities is ensured and the afterload is reduced.

The lateral holes can either be provided in all four quadrants of a cannula so that several holes lie on the same cross-sectional plane of the cannula. In addition, several holes, such as, for example, one to three holes, can be arranged in a row one behind the other.

Another form of embodiment envisages that in two quadrants (180°) or three quadrants (120°) one to three holes are arranged one behind the other in each case. However, two areas can be also provided each with three holes one behind the other, or holes which are offset by 90° with regard to each other.

Particularly in connection with the holes it is proposed that the cannula has a valve. Such a valve is preferably arranged in the area of the reduction in diameter. A preferred example of embodiment envisages a cannula with a valve, which comprises at least one and preferably several flaps.

Such a valve mechanism is based on the principle of the aortic valve with, for example, three leaflets. Preferably the base of the valve is arranged at the transition to the change in caliber. As result of the stronger flow during pump acceleration the valve opens. The ratio of relative flap opening to volumetric flow can be set through the positioning and design of the flap.

According to a preferred embodiment example the valve is located between the opening at the cannula tip and the lateral holes arranged in the cannula. Thus a partial flow of the perfusion is brought about through the cannula center to the cannula tip and another partial flow through the holes arranged in the cannula wall. The valve located between the lateral holes and the cannula tip can thereby vary these partial flows. With a narrowed valve the volumetric flow increases in the lateral holes and with an open valve the volumetric flow to the cannula tip increases.

A preferred example of embodiment envisages that the valve has at least one and preferably several flaps. These flaps can be arranged within the cannula in order to restrict the throughflow to the cannula tip within the cannula. It is advantageous if at least one flap has a spring mechanism. This spring mechanism can be achieved through a spring or through the selection of material and design of the flaps.

When using the cannula, during the phase of low throughflow through the cannula, for example during heart systole, the spring force of the valve can close the cannula or reduce the throughflow. Here the force of the volumetric flow acts against the spring force of the valve. If the force of the volumetric flow is less than the spring force of the value, the valve closes. If lateral holes are present, this results in the blood flow mainly being directed through the lateral holes and thus supplying the lower extremities for example. This takes place, for example with heart systole during a cardiogenic shock as it is too weak to open the valve, through which the lower extremities are better supplied with blood. Depending on the arrangement of the lateral holes the renal artery can also be supplied in this situation.

As a mechanism for closing the valve a passive mechanism can be envisaged in which the flow through the valve is reduced through the material stiffness of the flap at reduced volumetric flow. Alternatively or additionally a spring mechanism can be provided on the outer edges of the valve leaflet.

A further aspect of the invention envisages that on its inner side the cannula has, at least in sections, a spiral-shaped structure. Through such a structure the liquid flowing within the cannula can acquire a rotational movement which stabilizes the flow. This is advantageous particularly in connection with the tapering, the openings or the valve as any change on the inner side of the cannula influences the stable volumetric flow.

A spiral-shaped structure on the inner side of the cannula can for example be achieved through a spiral arrangement of the holes within the cannula. Alternatively or additionally it is however be envisaged that in accordance with the principle of a rifle barrel helical embossing is provided on the inner side of the cannula. According to a first embodiment example the structure is in the form of an elevation. For this, for example, a spiral-shaped or multiple thread structure is provided that penetrates convexly into the interior of the volume. Such a structure can be incorporated into or applied to the inner wall of the cannula. In doing so mixed forms between convex and concave cannula areas can be provided which are produced by application and removal on the inner wall of the cannula or a corresponding design of the inner all of the cannula.

The structure can extend within the cannula over the entire cannula length or over only part of the cannula length. For example in the direction of flow the structure can only be provided in the last third of the insertion length in order to only give the medium flowing in the cannula a rotational movement there.

The incline of the spiral-shaped structure brings about the relevant rotational movement. The incline of the structure can be given as sine α (cannula length divided by cannula diameter) or as sine α of the reciprocal value. This results in an incline=sine α (cannula length divided by diameter) or an incline=sine α (1 divided by cannula length or diameter).

A special variant envisages that the structure is formed by a wire reinforcement of the cannula. A wire reinforcement provided within the cannula can be helical and result in a corresponding spiral structure within the cannula which brings about a rotational movement within the cannula.

BRIEF DESCRIPTION OF THE DRAWINGS

Examples of embodiments of cannulas according to the invention are shown in the drawing and will be described in more detail below. In this:

FIG. 1 shows a side view of a cannula with tapering and a prolonged tip,

FIG. 2 shows a side view of a cannula with a conical tip,

FIG. 3 shows a side view of a cannula with several holes on its circumference,

FIG. 4 shows a side view of a cannula with holes arranged offset with regard to each other on the circumference FIG. 5 schematically shows the function of an open valve in a partially cross-sectional side view, FIG. 6 schematically shows a front view of the valve shown in FIG. 5, FIG. 7 schematically shows a side view of a partially closed valve, FIG. 8 schematically shows a front view of the valve shown in FIG. 7, FIG. 9 schematically shows a cross-section through a cannula with a convex spiral-shaped elevation, FIG. 10 schematically shows a cross-section through a cannula with two opposite spiral-shaped elevations and FIG. 11 schematically shows a cross-section through a cannula with four concavely designed spiral-shaped recesses.

DETAILED DESCRIPTION OF THE PREFERRED EMBODIMENTS

The cannula 1 shown in FIG. 1 has a cylindrical basic body 2, a cylindrical cannula tip 3 and in between as a diameter reduction concave tapering 4 which forms a transition between the cylindrical basic body 2 with the larger diameter and the cylindrical tip 3 with the smaller diameter. The position of the tapering 4 is selected so that the length 5 is two thirds of the cannula or insertion length.

FIG. 2 shows an alternative front end of the cannula 6 in which a conical tapering 7 forms the front end of the cannula 6 so that the cannula 6 has a conical cannula tip with length 8.

Holes 9, 10 can be provided within the cannula and preferably in the basic body 2 of the cannula with the larger diameter. FIG. 3 shows an arrangement of holes each offset by 90° in the longitudinal direction of the cannula. In the example of embodiment there are thus four rows 11, 12 of holes slightly offset with regard to each other, each of which has three holes 13-15, 16-18 and 19-21.

In the embodiment example shown in FIG. 4 the entire rows 22, 23, 24 are each arranged offset with regard to each other. In the embodiment example each of the rows has three holes. However, two or more holes can also be provided.

In the valve 30 shown in FIGS. 5-8 three valve leaflets 34, 35, 36 are provided in the tapering area 31 between a cannula section 32 with a larger diameter and a cannula section 33 with a smaller diameter, which are attached to the inner wall of the cannula in the tapering area 31. These valve leaflets 34-36 are opened by a volumetric flow 37 so that an opening 38 comes about through which a fluid can flow from cannula section 32 to cannula section 33.

If the pressure of the volumetric flow 37, as shown in FIGS. 7 and 8 decreases the valve leaflets 34-36 are forced inwards through their material stiffness so that the opening 38 closes in that the valve leaflets 34-36 are in contact with each other at point 39 and hinder or stop the throughflow.

Different variants for applying a rotating movement within the cannula are shown in FIGS. 9-11. These are only schematically shown embodiment variants for indicating the possibility of applying a rotating movement within the cannula. FIG. 9 shows a cannula 40 with an elevation 41 bulging radially inwards which extends in a helical manner within the cannula. A double-threaded form of embodiment is shown in FIG. 10. Here, a first elevation 43 and a second elevation 44 opposite the elevation 43 are provided within the cannula 42. Both elevations form part of a double-threaded spiral formed within the cannula 42.

In FIG. 11, using the example of four recesses, it is shown how a rotating movement can be applied to a fluid being conveyed in the cannula by means of recesses 45-48 within the cannula 49.

The invention claimed is:

1. An arterial cannula comprising:
   a tip;
   an outlet;
   a first cylindrical cannula section having a first internal diameter from 15 Fr to 19 Fr;
   a second cylindrical cannula section having a second internal diameter from 13 Fr to 17 Fr;
   a diameter reduction section forming a caliber narrowing transition between the first and second cylindrical cannula sections; and
   a valve having at least one flap arranged in the diameter reduction section;
   wherein the arterial cannula has an insertion length,
   wherein the diameter reduction section is located 25% to 40% of the insertion length away from the tip of the arterial cannula to enable the arterial cannula to be inserted past a branching area of a blood vessel without blocking blood flow to surrounding branches of the blood vessel.

2. The arterial cannula according to claim 1, wherein the arterial cannula has lateral holes and the diameter reduction section is arranged between the lateral holes and the tip of the arterial cannula.

3. The arterial cannula according to claim 1, wherein the valve has several flaps.

4. The arterial cannula according to claim 1, wherein the at least one flap has a spring mechanism.

5. The arterial cannula according to claim 2, wherein one base of the at least one flap is arranged in the diameter reduction section.

6. The arterial cannula according to claim 1, wherein the diameter reduction section is in the form of a conically tapering section.

7. The arterial cannula according to claim 1, wherein a conical end of the tip has a length which is shorter than that of the internal diameter of the area of the arterial cannula adjoining the tip.

8. The arterial cannula according to claim 1, the insertion length is 20 to 50 cm.

9. The arterial cannula according to claim 1, wherein on an inner side of the arterial cannula, at least in sections, the arterial cannula comprises a spiral-shaped structure.

10. The arterial cannula according to claim 9 wherein the spiral-shaped structure is an elevation.

11. The arterial cannula according to claim 9, wherein the spiral-shaped structure is a recess.

12. The arterial cannula according to claim 9, wherein the spiral-shaped structure is multiple-threaded.

13. The arterial cannula according to claim 9, wherein the spiral-shaped structure is formed by a wire reinforcement of the arterial cannula.

\* \* \* \* \*